United States Patent [19]

Rollins et al.

[11] Patent Number: 5,278,287
[45] Date of Patent: Jan. 11, 1994

[54] HUMAN CYTOKINE

[75] Inventors: Barrett Rollins, Brookline; Charles Stiles, Newton Center; Gordon G. Wong, Jamaica Plain, all of Mass.

[73] Assignees: Genetics Institute, Inc., Cambridge; Dana-Farber Cancer Institute, Boston, both of Mass.

[21] Appl. No.: 46,243

[22] Filed: Apr. 13, 1993

Related U.S. Application Data

[62] Division of Ser. No. 351,008, May 12, 1989, Pat. No. 5,212,073.

[51] Int. Cl.$^5$ .................. C07K 3/00; C07K 15/00; C12P 21/06; C12N 5/00
[52] U.S. Cl. .................. 530/351; 530/324; 530/350; 536/23.1; 536/23.2; 536/23.5; 536/23.51; 536/23.52; 435/69.1; 435/69.5; 435/240.2; 435/252.3; 435/320.1
[58] Field of Search .................. 435/69.5, 69.1, 240.2, 435/252.3, 320.1; 536/23.1, 23.2, 23.4, 23.5, 23.51, 23.52, 23.53; 530/324, 350, 351

[56] References Cited

U.S. PATENT DOCUMENTS 4,399,216  8/1983  Axel et al. .................. 435/6
4,477,571  10/1984  Chang et al. .................. 435/253

FOREIGN PATENT DOCUMENTS

WO90/078-
   63  7/1990  PCT Int'l Appl. .
WO90/087-
   77  8/1990  PCT Int'l Appl. .
WO90/08778  8/1990  PCT Int'l Appl. .

OTHER PUBLICATIONS

Anthony J. Valente et al., Biochemistry 27:4162–4168 (1988).
D. T. Graves et al., Science 245:1490–1493 (1989).
Elizabeth A. Robinson et al., Proc. Natl. Acad. Sci. U.S.A. 86:1850–1854 (1989).
Barrett J. Rollins et al., Molecular and Cellular Biology 11(6):3125–3131 (1991).
Biochemical and Biophysical Research Communications (Feb. 28, 1989) Furutani et al. vol. 159, No. 1, pp. 249–255.
FEBS Letters (Feb. 1989), Yoshimura et al., vol. 244, No. 2, pp. 487–493.
Cell (1983), Cochran et al, vol. 33, pp. 939–947.
PNAS (1986), Rittling et al. vol. 83, pp. 3316–3320.
PNAS (Mar. 1989), Robinson et al. vol. 86 pp. 1850–1854.
Science (Nov. 1987), Rollins et al. vol. 238, pp. 1269–1271.

*Primary Examiner*—Robert J. Hill, Jr.
*Assistant Examiner*—Gian P. Wang
*Attorney, Agent, or Firm*—Julia D. Hart

[57] ABSTRACT

A novel human cytokine, JE factor, and processes for producing it are disclosed. JE may be used in pharmaceutical preparations for stimulating and/or enhancing immune responsiveness and in wound healing and related tissue repair. containing the factor.

2 Claims, No Drawings

HUMAN CYTOKINE

This is a divisional application of pending U.S. application Ser. No. 07/351,008, filed May 12, 1989, now U.S. Pat. No. 5,212,073.

The present invention relates to a novel cytokine that is important in host defense and immunity against infection and for the processes for obtaining the purified factor by recombinant genetic engineering techniques.

BACKGROUND OF THE INVENTION

A family of regulatory proteins that deliver signals between many different types of cells in the body has been identified. These regulatory molecules are known as cytokines. Many of the cytokines have been found to control the growth and development and biological activities of cells in the hematopoietic and immune systems. Cytokines have also been identified which are produced by other cell types including fibroblasts and endothelial cells which transmit signals between these cells and a variety of responsive target cells. This family of cytokines is clearly important for maintaining homeostasis and for coordinating the physiological responses to a variety of insults including wounding and infection as well as regulating the immune response [See, for example G. Wong & S. Clark, *Immunology Today*, 9(5):139 (1988)]. The family of cytokines includes the interleukins,, the hematopoietic colony-stimulating factors, the interferons,, and the tumor necrosis factors among others. In addition, two subfamilies within the larger cytokine family have emerged that share evolutionary relatedness at the nucleotide level. Members of one of these families share sequence similarity with a cytokine known as macrophage inflammatory protein 1 (MIP-1) [Davatelis, G. et al *J. Exy. Med.*, 167:1939-1944 (1988) ], while members of the other family share sequence similarity with a second macrophage inflammatory protein, MIP-2 [Wolpe, S. D. et al, *Proc. Nat'l Acad. Sci. USA*, 86:612-616 (1988)]. MIP-1 and MIP-2 are cytokines produced by activated macrophages that induce local inflammatory responses when injected subcutaneously in mice. Other polypeptides have been identified through molecular biological approaches which are clearly related to either MIP-1 or MIP-2 but for which biological activities have not yet been identified. Although the function of these molecules is not known, they, like other members of the cytokine family, are likely to be important in various aspects of regulating homeostasis or coordinating physiological responses to wounding, injury, or infection or in the regulation of the immune system.

One member of the MIP-1 subfamily may be the murine JE [Rollins et al, *Proc. Nat'l Acad. Sci. USA* 85:3738-3752 (1988)] and its human homolgue disclosed herein.

BRIEF SUMMARY OF THE INVENTION

In one aspect the present invention provides, substantially free from co-produced polypeptides, a novel human cytokine herein termed JE which is elicited in response to platelet-derived growth factor (PDGF). JE may be characterized by containing the predicted amino acid sequence from at least amino acid #30 to #99 as set forth in Table I. This novel factor when expressed in COS cells displays considerable size heterogeneity with three predominant species present with estimated sizes of approximately 15,500, 15,000, and 13,000 as determined by SDS-PAGE. Additional microheterogeneous species are present with molecular weights from 16,000-18,000 daltons.

In one aspect, the invention provides JE factor produced by culturing a cell transformed with the DNA sequence comprising the sequence of Table I from at least nucleotide #73 to #772 and recovering and purifying from the culture medium a protein comprising the amino acid sequence from amino acid #30 to #99 of Table I.

Another aspect of the invention includes DNA sequences coding on expression for a human JE polypeptide. One such DNA sequence is the same or substantially the same as the approximately 772 nucleotide sequence which appears below in Table I.

Also provided by the present invention are vectors containing a DNA sequence encoding JE in operative association with an expression control sequence. Host cells transformed with such vectors for use in producing recombinant JE are also provided by the present invention.

The vectors and transformed cells of the invention are employed in another aspect, a novel process for producing recombinant human JE polypeptide. In this process a cell line transformed with a DNA sequence encoding JE polypeptide in operative association with an expression control sequence therefor is cultured. This claimed process may employ a number of known cells as host cells for expression of the polypeptide. Presently preferred cell lines are mammalian cell lines and bacterial cells.

Another aspect of this invention provides pharmaceutical compositions comprising a therapeutically effective amount of JE in a pharmaceutically acceptable vehicle. Because JE expression is activated by PDGF, a growth f actor released by platelets at the site of a wound, JE protein is likely to be useful directly for treating wounds. JE is also likely to have other cytokine properties including the ability to enhance host defense or to stimulate the hematopoietic or immune systems. Therefore, the pharmaceutical compositions of the invention may be useful in the treatment of cancer or in potentiating the efficacy of vaccines. Generally, it is contemplated that compositions of the invention may be useful for the treatment of disease states which involve immune system deficiencies.

A further aspect of the invention, therefore, is a method for treating tissue injuries or accelerating wound healing by administering to a patient a therapeutically effective amount of JE in a suitable pharmaceutical carrier. Further included are methods for treating cancer, diseases characterized by a deficiency in the number or level of activity of hematopoietic cells, or potentiating the efficacy of vaccines by administering to a patient a therapeutically effective amount of JE in a suitable pharmaceutical carrier. These therapeutic methods may include administering simultaneously or sequentially with JE polypeptides an effective amount of at least one other cytokine, hematopoietin, interleukin, growth factor, or antibody.

other aspects and advantages of the present invention will be apparent upon consideration of the following detailed description of preferred embodiments thereof.

DETAILED DESCRIPTION OF THE INVENTION

The novel human cytokine, JE factor, provided by the present invention is a homogeneous polypeptide or proteinaceous composition substantially free of association with other co-produced mammalian proteinaceous materials. It is characterized by containing the amino acid sequence from amino acid #30 to amino acid #99 as set forth in Table I. This protein can be produced via recombinant techniques to enable large quantity production of pure, active JE useful for therapeutic applications. Recombinant human JE factor expressed in mammalian cells displays apparent molecular weight predominant species of 15,500, 15,000, and 13,000 daltons (±2,000 daltons)as determined by sodium dodecylsulfate polyacrylamide gel electrophoreseis (SDS-PAGE) under non-reducing conditions. Additional microheterogeneous protein species are present from 16,000–18,000 daltons (±2,000 daltons).

Allelic variations of the DNA sequence of Table I encoding JE factor described above are also included in the present invention as well as analogs or derivatives thereof. Thus the present invention also encompasses these novel DNA sequences, free of association with DNA sequences encoding other primate proteins, and coding on expression for JE polypeptides. These DNA sequences include those sequences which hybridize under stringent hybridization conditions [see, T. Maniatis et al, *Molecular Cloning* (*A Laboratory Manual* ), Cold Spring Harbor Laboratory (1982), pages 387 to 389] to the DNA sequence of Table I. An example of one such stringent hybridization condition is hybridization at 4XSSC at 65° C., followed by a washing in 0.1XSSC at 65° C. for an hour. Alternatively an exemplary stringent hybridization condition is in 50% formamide, 4XSSC at 42° C.

DNA sequences which hybridize to the sequence for JE under relaxed hybridization conditions and which code on expression for JE peptides having JE biological properties also encode novel JE polypeptides. Examples of such non-stringent hybridization conditions are 4XSSC at 50° C. or hybridization with 30–40% formamide at 42° C. For example, a DNA sequence which shares regions of significant homology, e.g., sites of glycosylation or disulfide linkages, with the sequences of JE and encodes a protein having one or more JE biological properties clearly encodes a JE polypeptide even if such a DNA sequence would not stringently hybridize to the JE sequence of Table I.

Similarly, DNA sequences which code for JE polypeptides coded for by the sequence of JE, but which differ in codon sequence due to the degeneracies of the genetic code or allelic variations (naturally-occurring base changes in the species population which may or may not result in an amino acid change) are also encompassed by this invention. Variations in the DNA sequence of JE which are caused by point mutations or by induced modifications to enhance the activity, half-life or production of the polypeptides encoded thereby are also encompassed in the invention.

The JE polypeptides provided herein also include factors encoded by sequences similar to those of purified recombinant JE, but into which modifications are naturally provided (e.g. allelic variations in the nucleotide sequence which may result in amino acid changes in the polypeptide) or deliberately engineered. Modifications in the peptide or DNA sequence can be made by one skilled in the art using known techniques. Modifications of interest in the JE sequences may include the replacement, insertion or deletion of a selected amino acid residue in the coding sequence. Mutagenic techniques for such replacement, insertion or deletion are well known to one skilled in the art. [See, e.g., U.S. Pat. No. 4,518,584.]

Other specific mutations of the sequence of the JE polypeptide described herein may involve modifications of a glycosylation site. The absence of glycosylation or only partial glycosylation results from amino acid substitution or deletion at any asparagine-linked glycosylation recognition site or at any site of the molecule that is modified by addition of O-linked carbohydrate. An asparagine-linked glycosylation recognition site compresses a tripetide sequence which is specifically recognized by appropriate cellular glycosylation enzymes. These tripetide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripetide sequence. Expression of such altered nucleotide sequences produces variants which are not glycosylated at that site.

Other analogs and derivatives of the sequence of JE which would be expected to retain JE activity in whole or in part may also be easily made by one of skill in the art given the disclosures herein. One such modification may be the attachment of polyethylene glycol onto existing lysine residues, or the insertion of lysine residues in the sequence for attachment of PEG moieties. Such modifications are believed to be encompassed by this invention.

Further included in the present invention are synthetic polypeptides which duplicate or partially duplicate continuous sequences of the amino acid residues of Table I. The synthetically-constructed JE polypeptide sequences, by virtue of sharing primary, secondary, or tertiary structural and conformational characteristics with JE polypeptides may possess JE biological properties in common therewith. Thus, they may be employed as biologically active or immunological substitutes for natural, purified JE polypeptides in therapeutic and immunological processes. These JE polypeptides may be produced by known conventional chemical synthesis. Methods for constructing the polypeptides of the present invention by synthetic means are known to those of skill in the art.

The present invention also provides a method for producing JE polypeptides. Having identified the CDNA it is introduced into an expression vector to make an expression system for JE. A selected host cell is transformed with the vector and cultured. The method of the present invention therefore comprises culturing a suitable cell or cell line, which has been transformed with a DNA sequence coding on expression for JE polypeptide under the control of known regulatory sequences. The expressed factor is then recovered, isolated and purified from the culture medium.

Suitable cells or cell lines may be mammalian cells, such as Chinese hamster ovary cells (CHO) or 3T3 cells. The selection of suitable mammalian host cells and methods for transformation, culture, amplification, screening and product production and purification are known in the art. See, e.g., Gething and Sambrook, *Nature,* 293:620–625 (1981), or alternatively, Kaufman et al, *Mol. Cell. Biol.,* 5(7):1750–1759 (1985) or Howley et al, U.S. Pat. No. 4,419,446. Other suitable mammalian cell lines, are the monkey COS-1 cell line, and the CV-1 cell line. Further exemplary mammalian host cells include particularly primate cell lines and rodent cell lines, including transformed cell lines. Normal diploid cells, cell strains derived from in vitro culture of primary tissue, as well as primary explants, are also suitable. Candidate cells need not be genotypically deficient in the selection gene so long as the selection gene is dominantly acting. Other suitable mammalian cell lines include but are not limited to HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of *E. coli* (e.g., HB101, MC1061 and strains used in the following examples) are well-known as host cells in the field of biotechnology. Various strains of *B. subtilis*, PseudoNonas, other bacilli and the like may also be employed in this method.

Many strains of yeast cells known to those skilled in the art are also available as host cells for expression of the polypeptides of the present invention. Additionally, where desired, insect cells may be utilized as host cells in the method of the present invention. See, e.g. Miller at al, *Genetic Engineering*, 8:277-298 (Plenum Press 1986) and references cited therein.

The present invention also provides vectors for use in the method of expression of novel JE polypeptides. These vectors contain the novel JE DNA sequences which code for JE polypeptides of the invention. Alternatively, vectors incorporating modified sequences as described above are also embodiments of the present invention and useful in the production of JE polypeptides. The vector employed in the method also contains selected regulatory sequences in operative association with the DNA coding sequences of the invention and capable of directing the replication and expression thereof in selected host cells. The vector used in the examples below is pXM [Y. C. Yang et al, *Cell*, 47:3-10 (1986)]. The mammalian cell expression vectors described herein may be synthesized by techniques well known to those skilled in this art. The components of the vectors, e.g. replicons, selection genes, enhancers, promoters, and the like, may be obtained from natural sources or synthesized by known procedures. See, Kaufman et al, *J. Mol. Biol.*, 159:511-521 (1982): and Kaufman, *Proc. Natl. Acad. Sci., USA*, 82:689-693 (1985). Alternatively, the vector DNA may include all or part of the bovine papilloma virus genome [Lusky et al, *Cell*, 36:391-401 (1984)] and be carried in cell lines such as C127 mouse cells as a stable episomal element. The transformation of these vectors into appropriate host cells can result in expression of the JE polypeptides. Other appropriate expression vectors of which numerous types are known in the art for mammalian, insect, yeast, fungal and bacterial expression can also be used for this purpose.

JE, purified to homogeneity from cells or produced recombinantly or synthetically, may be used in a pharmaceutical preparation or formulation to enhance host defense generally and may be employed in the treatment of many diseased states involving immune system deficiencies. They may be employed in methods for treating cancer and other disease. In its utility in stimulating host defense, JE may be used to treat pathological states resulting from disease, exposure to radiation or drugs, physical damage and trauma. These include for example, leukopenia, bacterial and viral infections, anemia, B cell or T cell deficiencies such as immune cell or hematopoietic cell deficiency following a bone marrow transplantation. JE may also be used to potentiate the immune response to a variety of vaccines creating longer lasting and more effective immunity. Because of its expression by PDGF-treated fibroblasts, we expect that JE may be useful in accelerating wound healing or other tissue repair.

Furthermore, subsequent to our discovery of the JE factor another group identified the same protein by its ability to serve as a monocyte chemoattractant [Yoshimura, T., et al, *FEBS Letters* 244:487-493 (1989)]. This activity of JE supports the expectation that JE factor may be useful in wound healing. Therapeutic treatment of wounds and diseases with these JE polypeptide compositions may avoid undesirable side effects caused by treatment with presently available drugs. Other uses for these novel polypeptides are in the development of monoclonal and polyclonal antibodies generated by standard methods for diagnostic or therapeutic use.

The polypeptides of the present invention may also be employed, alone or in combination with other cytokines, hematopoietins, interleukins, growth factors or antibodies in therapeutic treatment of the above-identified conditions, for example in the enhancement of host defense treatment of wounds or disease states.

Therefore, as yet another aspect of the invention are methods and therapeutic compositions for treating the conditions referred to above. Such compositions comprise a therapeutically effective amount of a JE polypeptide of the present invention in admixture with a pharmaceutically acceptable carrier. This composition can be systematically administered parenterally. Alternatively, the composition may be administered intravenously. If desirable, the composition may be administered subcutaneously or topically at the site of a wound. When systematically administered, the therapeutic composition for use in this invention is in the form of a pyrogen-free, paranterally acceptable aqueous solution. The preparation of such a pharmaceutically acceptable protein solution, having due regard to pH, isotonicity, stability and the like, is within the skill of the art.

The dosage regimen involved in a method for treating the above described conditions will be determined by the attending physician considering various factors which modify the action of drugs, e.g. the condition, body weight, sex and diet of the patient, the severity of any infection, time of administration and other clinical factors. Generally, the daily regimen should be in the range of 1-1000 micrograms of polypeptide per kilogram of body weight.

The therapeutic method and compositions of the present invention may also include co-administration with other human factors. Exemplary cytokines or hematopoietins for such use include the known factors IL-1, IL-2, IL-3, IL-4, IL-6, GM-CSF, G-CSF, M-CSF, MIF, Meg-CSF, the interferons, and erythropoietin. Other potential candidates f or participation in JE therapy may also include IL-4, G-CSF, CSF-1 or erythropoietin. Growth factors like B cell growth factor, B cell differentiation factor, or eosinophil differentiation factors may also prove useful in co-administration with JE. The dosage recited above would be adjusted to compensate for such additional components in the therapeutic composition. Progress of the treated patient can be monitored by conventional methods.

The following examples illustratively describe the cloning and production of human JE and other methods and products of the present invention. These examples are for illustration and do not limit the scope of the present invention.

EXAMPLE I

Cloning of Human JE

To obtain the cloned sequence for human JE, the full murine sequence is employed as a probe [Rollins et al, supra incorporated herein by reference for disclosure of the murine JE sequence] to screen a cDNA library prepared from the human fibroblast cell line, WI-38 (commercially available from the American Type Culture Collection, Rockville, Md., under accession number ATCC CCL75). This cell line produces a mixture of cytokines in response to stimulation with PDGF. JE factor may also be produced by other human cell lines.

The CDNA is synthesized using standard techniques. RNA is isolated using the quanidinium isothiocyanate method [Chirgwin et al *Biochemistry*, 18: 5294-5299 (1979)] from WI-38 cells treated with 10% BCS for 4 hrs. Poly(A)+ RNA is selected using a modification of the RNase H method [Gubler and Hoffman, *Gene*, 25 25:263-269 (1983)] as described in Yang et al, supra. The cDNA is cloned into pXM (Yang et al supra) and the DNA is used to transform competent *E. coli*. This vector permits the expression of CDNA inserts in mammalian cells, e.g. COS-1 cells. pXM contains the SV40 enhancer, major adenovirus late promoter, DHFR coding sequence, SV40 late message poly A addition site and VaI gene.

Recombinants from this library are plated and duplicate nitrocellulose replicas made of the plates. Approximately 40,000 colonies are screened with a EcoRI fragment of the the murine JE cDNA (Rollins et al, supra) labeled with $^{32}P$ using the random priming labeling technique [A. P. Feinberg and B. Vogelstein, *Anal. Biochem.* 132:6-13 (1983)]. Hybridization is carried out as described (Rollins et al, supra) except that the filters are washed in 1x standard saline citrate (SSC; 150 mM NaCl, 15 mM Na citrate, pH 7.0) at 55° C. for 1 hr. The filters are then washed in 0.2xSSC at the same temperature until the background radioactivity is lowered to an acceptable level to permit detection of specifically hybridizing sequences.

Twenty colonies hybridize to the probe. Upon rescreening thirteen duplicate positive clones are identified and six are examined. These six cDNA clones were similar based on restriction endonuclease mapping experiments and analysis. The nucleotide sequence and predicted amino acid sequence of one of the clones is set forth in Table I below. The nucleotide sequence is comprised of 772 base pairs. This sequence contains a single long open reading frame predicting a 99 amino acid polypeptide. The first 29 of these encode a hydrophobic peptide with characteristics of mammalian peptide secretory signals. Thus human JE is first synthesized as a precursor of 99 amino acids that gets proteolytically cleaved, possibly after residue 29, to yield a mature 70 amino acid polypeptide beginning with the sequence Ala-Pro. On the other hand, the hydrophobic leader sequence may be cleaved during processing after amino acid 23 [von Heijne, *Nucleic Acids Res.* 14:4683-4690 (1986)].

TABLE I

```
       10         20         30         40         50         60         70
CTCGAGCTGC AGAGCTAGCT CTGCAGCGAA ACATCCAATT CTCAAACTGA AGCTCGCACT CTCGCCTCCA 81              90          99         108         117
    >
GC  ATG AAA GTC TCT GCC GCC CTT CTG TGC CTG CTG CTC ATA GCA GCC ACC TTC
    MET Lys Val Ser Ala Ala Leu Leu Cys Leu Leu Leu Ile Ala Ala Thr Phe
    (1)

126        135         144         153         162         171
ATT CCC CAA GGG CTC GCT CAG CCA GAT GCA ATC AAT GCC CCA GTC ACC TGC TGC
Ile Pro Gln Gly Leu Ala Gln Pro Asp Ala Ile Asn Ala Pro Val Thr Cys Cys 180        189         198         207         216         225
TAT AAC TTC ACC AAT AGG AAG ATC TCA GTG CAG AGG CTC GCG AGC TAT AGA AGA
Tyr Asn Phe Thr Asn Arg Lys Ile Ser Val Gln Arg Leu Ala Ser Tyr Arg Arg 234        243         252         261         270         279
ATC ACC AGC AGC AAG TGT CCC AAA GAA GCT GTG ATC TTC AAG ACC ATT GTG GCC
Ile Thr Ser Ser Lys Cys Pro Lys Glu Ala Val Ile Phe Lys Thr Ile Val Ala 288        297         306         315         324         333
AAG GAG ATC TGT GCT GAC CCC AAG CAG AAG TGG GTT CAG GAT TCC ATG GAC CAC
Lys Glu Ile Cys Ala Asp Pro Lys Gln Lys Trp Val Gln Asp Ser MET Asp His 342        351         360         369  >      379         389        399
CTG GAC AAG CAA ACC CAA ACT CCG AAG ACT TGAACACTCA CTCCACAACC CAAGAATCTG
Leu Asp Lys Gln Thr Gln Thr Pro Lys Thr
                                    (99)

409        419         429         439         449         459        469
CAGCTAACTT ATTTTCCCCT AGCTTTCCCC AGACACCTTG TTTTATTTTA TTATAATGAA TTTTGTTTGT 479        489         499         509         519         529        539
TGATGTGAAA CATTATGCCT TAAGTAATGT TAATTCTTAT TTAAGTTATT GATGTTTTAA GTTTATCTTT 549        559         569         579         589         599        609
CATGGTACTA GTGTTTTTTA GATACAGAGA CTTGGGGAAA TTGCTTTTCC TCTTGAACCA CAGTTCTACC
```

TABLE I-continued

```
     619        629        639        649        659        669        679
CCTGGGATGT TTTGAGGGTC TTTGCAAGAA TCATTAATAC AAAGAATTTT TTTTAACATT CCAATGCATT 689        699        709        719        729        739        749
GCTAAAATAT TATTGTGGAA ATGAATATTT TGTAACTATT ACACCAAATA AATATATTTT TGTAAAAAAA 759        769
AAAAAAAAAA AAAAAAAAAA AAA
```

The amino acid sequence of JE set forth in Table indicates that it is member of the subfamily of cytokines related to MIP-1. Comparison of the amino acid and nucleotide sequence of human JE with that of murine JE (Rollins et al, supra) indicates that the proteins are closely related.

The JE genomic sequence is isolated using standard techniques. 500,000 plaques of a WI-38 genomic DNA library are screened using the human JE cDNA. Three plaques hybridize to the cDNA probe through triplicate plaque purification. The DNA is analyzed by blotting to nitrocellulose, and the EcoRI fragments hybridizing to hJE cDNA are subcloned into pGEM-7Zf(+)[Promega, Corp., Madison, Wis.]. Double stranded DNA is centrifuged and the supernatant analyzed by SDS-polyacrylamide gel electrophoresis.

EXAMPLE II

Expression of Recombinant Human JE

To produce JE, the cDNA encoding it as shown in Table I from at least nucleotide #73 to nucleotide #772, is transferred into an appropriate expression vector using techniques known to those skilled in the art. The vector is then introduced into the selected host cells by conventional genetic engineering techniques. The transformed cells are cultured and the expressed JE is recovered and purified from the culture medium using standard techniques.

A. Mammalian Cell Expression

To obtain expression of the JE polypeptide in mammalian host cells, the pXM vector (Yang et al supra) containing the JE DNA sequence is transfected into COS cells using the DEAE-dextran/chloroquine technique [Luthman and Magnusson, Nucl. Acids Res. 11: 1295-1308 (1983); and Sompayrac and Danna, PNAS 78:7575-7578 (1981)]. The size of the secreted proteins is described below in Example III. For stable integration of the vector DNA, and for subsequent amplification of the integrated vector DNA, both by conventional methods, CHO cells are employed.

1. Construction of CHO Cell Lines Expressing High Levels of JE

One method for producing high levels of the JE polypeptides of the invention from CHO mammalian cells involves the construction of cells containing multiple copies of the heterologous JE gene. The heterologous gene can be linked to an amplifiable marker, e.g., the dihydrofolate reductase (DHFR) gene for which cells containing increased gene copies can be selected for propagation in increasing concentrations of methotrexate (MTX) according to the procedures of Kaufman & Sharp, J. Mol. Biol., (1982) supra. This approach can be employed with a number of different cell types.

For example, the pXM vector containing a JE gene in operative association with other plasmid sequences enabling expression thereof and the DHRF expression plasmid pAdA26SV(A)3 (Kaufman & Sharp, Mol. Cell Biol., 3(9):1598-1608 (1983) can be co-introduced into DHFR-deficient CHO cells, DUKX-BII, by calcium phosphate coprecipitation and transfection. DHFR expressing transformants are selected for growth in alpha media with dialyzed fetal calf serum, and subsequently selected for amplification by growth in increasing concentrations of MTX (Sequential steps in 0.02, 0.2, 1.0 and 5 uM MTX) as described in Kaufman et al, Mol. Cell Biol., 5:1750 (1983). JE polypeptide expression is expected to increase with increasing levels of MTX resistance.

Stable transformants are then screened for expression of the product by standard immunological or enzymatic assays. The presence of the DNA encoding the JE polypeptides may be detected by standard procedures such as Southern blotting. Transient expression of the DNA encoding the polypeptides during the several days after introduction of the expression vector DNA into suitable host cells, such as COS-1 monkey cells, is measured without selection by activity or immunologic assay of the proteins in the culture medium.

One skilled in the art can also construct other mammalian expression vectors comparable to the pXM JE vector by, e.g., inserting the DNA sequence of JE from the respective plasmids with XhoI and employing well-known recombinant genetic engineering techniques and other known vectors, such as pJL3 and pJL4 [Gough et al., EMBO J., 4:645-653 (1985)] and pMT2 (starting with pMT2-VWF, ATCC #67122; see PCT application PCT/US87/00033). The transformation of these vectors into appropriate host cells can result in expression of the JE polypeptides.

B. Bacterial Expression Systems

Similarly, one skilled in the art could manipulate the sequence of JE by eliminating any mammalian regulatory sequences flanking the coding sequences and inserting bacterial sequences to create bacterial vectors for intracellular or extracellular expression of the JE polypeptides of the invention by bacterial cells. The DNA encoding the factor may be further modified to contain different codons for bacterial expression as is known in the art. Preferably the mature JE sequence (nucleotides 160 to 369 in Table I) is operatively linked in-frame to a nucleotide sequence encoding a secretory leader polypeptide permitting bacterial expression, secretion and processing of the mature variant protein, also as is known in the art. The compounds expressed in bacterial host cells may then be recovered, purified, and/or characterized with respect to physicochemical, biochemical and/or clinical parameters, all known methods.

C. Insect or Yeast Cell Expression

Similar manipulations can be performed for the construction of an insect vector [See, e.g., procedures described in published European patent application 155,476] for expression in insect cells. A yeast vector could also be constructed employing yeast regulatory sequences for intracellular or extracellular expression of the proteins of the present invention by yeast cells. [See, e.g., procedures described in published PCT application WO 86/00639 and European patent application EP 123,289.]

EXAMPLE III

Molecular Weight of JE Expressed in Mammalian Cells

COS cells transfected with pMX-JE are pulse labelled with $^{35}$S-methionine as described in Yang et al supra. 10 μl of the conditioned medium is fractionated on 10% polyacrylamide slab gels according to the method of Laemmli [Laemmli, V. R. *Nature* 227:680–685 (1970)]. The gels are impregnated with Enhance (New England Nuclear; Boston, Mass.), dried and exposed to X-Ray film. The transfected cells secrete three predominant proteins with molecular weights of approximately 15,500, 15,000, and 13,000 daltons as determined relative to low molecular weight protein standards (Pharmacia). There are additional microheterogeneous protein species with molecular weights from 16,000–18,000 daltons. These different forms most likely represent different glycosylation states of the same polypeptide.

The foregoing descriptions detail presently preferred embodiments of the invention. Numerous modifications and variations in practice of this invention are expected to occur to those skilled in the art. Such modifications and variations are within the following claims.

We claim:

1. A purified human JE factor polypeptide comprising an amino acid sequence from amino acid #30 to amino acid #99 of Table I.

2. The polypeptide according to claim 2 produced by the steps of a) culturing a cell transformed with a DNA sequence comprising the following sequence:

AT-
GAAAGTCTCGTCCGCCCTTCTGTGCCTGC-
TGCTCATAGCA GCCACCTTCATTCC-
CCAAGGGCTCGCTCAGCCAGATGCAAT-
CAATGCCCCAGTCACC
TGCTGCTATAACTTCACCAATAG-
GAAGATCCAGTGCAGAGGCTCGCGACGT-
GATAGA AGAATCACCAGCAGCAAGTGTC-
CCAAAGAAGCTGTGATCTTCAAGAC-
CATTGTGGCC AAGGAGATCTGTGCT-
GACCCCAAGCAGAAGTGGGTTCAGGATT-
CCATGGACCACCTG GACAAGCAAACC-
CAAACTCCGAAGACTTGAACACTCACT-
CCACAACCCAAGAATCTG CAGCTAACT-
TATTTTCCCCTAGCTTTCC-
CCAGACACCTTGTTTTATTTTATTATAAT
GAATTTTGTTTGTTGATGTGAAACAT-
TATGCCTTAAGTAATGTTAATTCTTATT-
TAA GTTATTGATGTTTTAAGTTTATCTTT-
CATGGTACTAGTGTTTTT-
TAGATACAGAGAC
TTGGGGAAATTGCTTTTCCTCTTGAAC-
CACAGTTCTACCCCTGGGATGTTTT-
GAGGG TCTTTGCAAGAATCAT-
TAATACAAAGAATTTTTTTTAACATT-
CCAATGCATTGCTAA AATATTATTGT-
GGAAATGAATATTTTGTAACTATTACAC-
CAAATAAATATATTTTTG
TAAAAAAAAAAAAAAAAAAAAAAAAAA-
AAAA a DNA sequence capable of hybridizing thereto; and b) recovering from said culture medium a protein comprising the amino acid sequence:

Ala Pro Val Thr Cys Cys Tyr Asn Phe Thr Asn Arg Lys Ile Ser Val Gln Arg Leu Ala Ser Tyr Arg Arg Ile Thr Ser Ser Lys Cys Pro Lys Glu Ala Val Ile Phe Lys Thr Ile Val Ala Lys Glu Ile Cys Ala Asp Pro Lys Gln Lys Trp Val Gln Asp Ser MET Asp His Leu Asp Lys Gln Thr Gln Thr Pro Lys Thr.

* * * * *